United States Patent
Hornung et al.

(10) Patent No.: US 10,588,594 B2
(45) Date of Patent: Mar. 17, 2020

(54) RECORDING AN IMAGE DATA RECORD WITH AN X-RAY IMAGING SYSTEM

(71) Applicant: Siemens Healthcare GmbH, Erlangen (DE)

(72) Inventors: Oliver Hornung, Dormitz (DE); Markus Kowarschik, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/101,419

(22) Filed: Aug. 11, 2018

(65) Prior Publication Data

US 2019/0046150 A1     Feb. 14, 2019

(30) Foreign Application Priority Data

Aug. 11, 2017 (EP) ..................................... 17185953

(51) Int. Cl.
*A61B 6/00* (2006.01)
*A61B 6/03* (2006.01)

(52) U.S. Cl.
CPC ............ *A61B 6/582* (2013.01); *A61B 6/4441* (2013.01); *A61B 6/4452* (2013.01);
(Continued)

(58) Field of Classification Search
CPC ..... A61B 6/582; A61B 6/4441; A61B 6/4452; A61B 6/4458; A61B 6/5205; A61B 6/56; A61B 6/032
(Continued)

(56) References Cited

U.S. PATENT DOCUMENTS

2004/0215071 A1* 10/2004 Frank ................... A61B 6/4441
                                                               600/407
2005/0025287 A1*  2/2005 Ritt ......................... A61B 6/00
                                                               378/207
(Continued)

FOREIGN PATENT DOCUMENTS

DE    102009061749 A1    6/2015
EP        2633817 A1    9/2015

OTHER PUBLICATIONS

European Search Report for corresponding Application No. 17185953.1-1124, dated Mar. 22, 2018, with English Translation. pp. 1-10.
(Continued)

*Primary Examiner* — Taeho Jo
(74) *Attorney, Agent, or Firm* — Lempia Summerfield Katz LLC

(57) ABSTRACT

A method for acquiring an image data record with an x-ray imaging system with a recording system that may be rotated around an examination object is provided. The recording system is embodied for an endless rotation. The method includes providing a calibration data record that has measurement data from a plurality of rotations of the recording system in endless rotation. At least one selectable acquisition parameter is received from the group consisting of: period of acquisition; number of projection images to be acquired; angular region of the acquisition to be recorded; and angular increment between every two sequential projection images. An acquisition protocol with the selected acquisition parameter(s) is determined from the provided calibration data record. The determined acquisition protocol is loaded, and an image data record is recorded using the determined acquisition protocol.

19 Claims, 2 Drawing Sheets

(52) U.S. Cl.
CPC .......... *A61B 6/4458* (2013.01); *A61B 6/5205* (2013.01); *A61B 6/56* (2013.01); *A61B 6/032* (2013.01)

(58) Field of Classification Search
USPC ........................................................ 378/197
See application file for complete search history.

(56) References Cited

U.S. PATENT DOCUMENTS

| | | | | |
|---|---|---|---|---|
| 2005/0213704 | A1* | 9/2005 | Ritt | A61B 6/00 378/62 |
| 2005/0232389 | A1* | 10/2005 | Klingenbeck-Regn | A61B 6/032 378/9 |
| 2008/0237507 | A1* | 10/2008 | Enomoto | A61B 6/583 250/582 |
| 2009/0028288 | A1* | 1/2009 | Horiuchi | A61B 6/032 378/4 |
| 2009/0046916 | A1* | 2/2009 | Matsuura | A61B 6/032 382/131 |
| 2009/0290771 | A1* | 11/2009 | Frank | A61B 6/4441 382/128 |
| 2011/0066022 | A1 | 3/2011 | Fadler et al. | |
| 2011/0135053 | A1* | 6/2011 | Noordhoek | A61B 6/583 378/11 |
| 2013/0235970 | A1* | 9/2013 | Voland | G01N 23/046 378/4 |
| 2015/0103970 | A1* | 4/2015 | Chen | G01N 23/046 378/5 |
| 2016/0203620 | A1* | 7/2016 | Zou | A61B 6/032 378/19 |
| 2016/0239971 | A1* | 8/2016 | Yu | A61B 6/032 |

OTHER PUBLICATIONS

European Search Report for corresponding Application No. 17185953.1-1124, dated Mar. 22, 2018.

* cited by examiner

RECORDING AN IMAGE DATA RECORD WITH AN X-RAY IMAGING SYSTEM

This application claims the benefit of EP17185953, filed on Aug. 11, 2017, which is hereby incorporated by reference in its entirety.

BACKGROUND

The present embodiments relate to recording an image data record with an x-ray imaging system.

In three-dimensional (3D) and four-dimensional (4D) x-ray imaging, x-ray imaging systems in which a recording system with an x-ray detector and an x-ray source is arranged on a bracket (e.g., a C-arm) and rotates around an examination object may be used, so that projection images may be recorded and reconstructed from a plurality of projection directions. A fundamental technical problem in such a setup lies in that a great deal of time (e.g., a number of days) is required in order to calibrate 3D and 4D acquisition protocols.

For example, angiographic 3D recordings are restricted due to the mechanical properties of the bracket. This restriction results in each 3D acquisition protocol having to be calibrated separately in advance. Protocols of this kind differ, for example, in the number of projection images, the angular region to be scanned, and the acquisition time. This of course necessitates a high level of outlay (e.g., combinatorics; for each parameter change, a new acquisition protocol is generally required). A concrete restriction of contemporary systems arises in that, for example, it is not possible to specify the acquisition time directly during an intervention due to the excessively high calibration outlay that results. Such a feature is desirable, however, with regard to methods such as, for example, 4D time-resolved three-dimensional digital subtraction angiography (DSA), in which the acquisition period ideally arises from physiological conditions (e.g., haemodynamics).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for recording an image data record with an x-ray imaging system that reduces the disadvantages of the prior art is provided. As another example, an x-ray device suitable for performing the method is provided.

By using the method according to one or more of the present embodiments for acquiring an image data record with an x-ray imaging system with a recording system that may be rotated around an examination object (e.g., configured for an endless rotation such as an unlimited rotatability in both directions), acquisition protocols may be calculated from calibration data already present in a simple manner, without having to perform a new calibration every single time the acquisition parameters are changed. The method includes providing a calibration data record that has measurement data from a plurality of rotations of the recording systems in endless rotation. At least one selectable acquisition parameter (e.g., from the group of period of acquisition, number of projection images to be acquired, angular region of the acquisition to be recorded, and angular increment between every two sequential projection images) is received. An acquisition protocol with the selected acquisition parameter(s) is determined (e.g., calculated) from the provided calibration data record. The determined acquisition protocol is loaded, and an image data record is recorded using the determined acquisition protocol. A prerequisite for this is formed by novel recording systems rotating in a particularly constant manner (e.g., C-arms), which may rotate with steady dynamics for each speed of rotation. Using the method according to one or more of the present embodiments, time and outlay for recalibrations may be saved, and 3D and 4D recordings may be performed flexibly and also, during interventions and in other time-critical applications, with freely selectable acquisition parameters. In this case, the calibration data record that is provided may contain measurement data of as many as possible or all possible speeds of rotation, including the subsamplings.

According to a further embodiment, at least one further acquisition parameter is received from the group consisting of period of acquisition, number of projection images to be acquired, angular region of the acquisition to be recorded, and angular increment between every two sequential projection images, a further acquisition protocol is calculated, the further acquisition protocol is loaded, and a further image data record is recorded therefrom. This may be performed immediately following the recording of the first image data record (e.g., when a change of an acquisition parameter is required during an interventional procedure).

According to a further embodiment, a user of the x-ray imaging system is queried regarding the selectable acquisition parameter from the group: period of acquisition, number of projection images to be acquired, angular region of the acquisition to be recorded, and angular increment between every two sequential projection images (e.g., by a display unit). In this case, the user is questioned directly regarding desired acquisition parameters and may subsequently input these, for example, by an input unit, so that the desired acquisition parameters may then be received by the x-ray imaging system. Alternatively, the acquisition parameters may also be selected and received automatically (e.g., based on requirements of the organ programs or other prerequisites). A flexible selection of the acquisition parameters is possible.

As an alternative to what is stated above, further acquisition parameters beyond the group consisting of period of acquisition, number of projection images to be acquired, angular region of the acquisition to be recorded, and angular increment between every two sequential projection images may also be received and used.

To perform the method, provision is made according to one or more of the present embodiments for an x-ray imaging system with an x-ray detector and an x-ray source, which are arranged on a bracket. The bracket is configured to rotate in an endless rotation (e.g., an unrestricted rotatability with regard to the angle of rotation) around an examination object, where the x-ray imaging system is configured to record a plurality of projection images from different projection directions and an image data record in accordance with an acquisition protocol during the rotation of the recording system. The x-ray imaging system includes a system controller configured to provide a previously recorded calibration data record that has measurement data from a plurality of rotations of the recording system in endless rotation. The system controller is also configured to load an acquisition protocol. The x-ray imaging system also includes an input unit configured for receiving at least one selectable acquisition parameter from the group consisting of period of acquisition, number of projection images to be acquired, angular region of the acquisition to be recorded, and angular increment between every two sequential projection images. The x-ray imaging system includes a computing unit configured to calculate an acquisition protocol with the selected acquisition parameter(s) from the provided calibration data record.

According to an embodiment, the bracket is formed by a C-arm, and the C-arm is suspended by a slip ring structure so that an endless rotation of the C-arm may be achieved.

In one embodiment, the x-ray imaging system has a display unit for displaying a query relating to the acquisition parameter(s), and an input unit for inputting the corresponding acquisition parameters.

DETAILED DESCRIPTION

Figure 1:
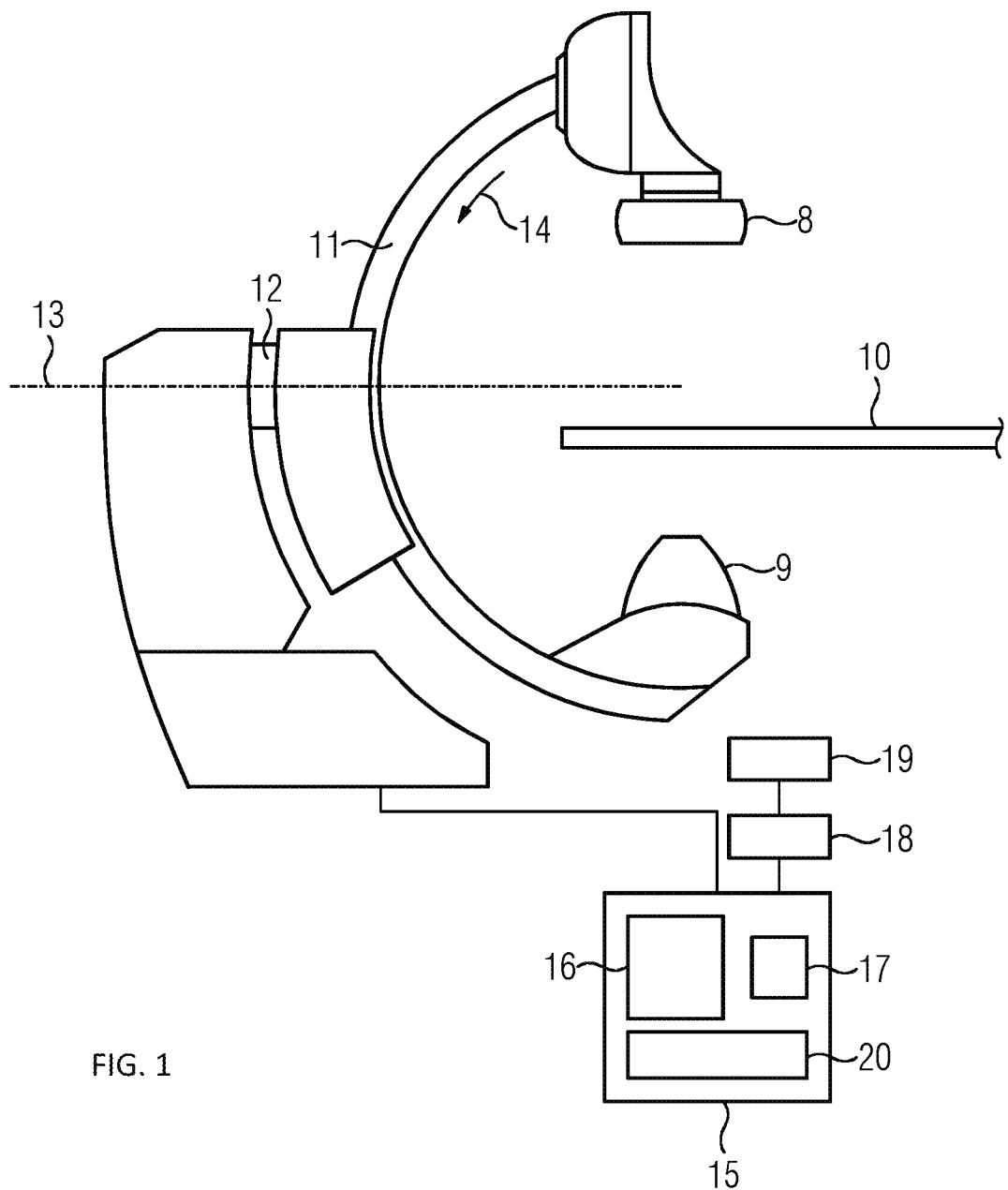
FIG. 1 shows a view of one embodiment of an x-ray imaging system.

In FIG. 1, an exemplary x-ray imaging system with a C-arm 11 that is suitable for performing a method of one or more of the present embodiments is shown. An x-ray source 9 is arranged on one end of the C-arm 11, and an x-ray detector 8 is arranged on the other end of the C-arm 11. The C-arm 11 may be moved in multiple planes (e.g., the C-arm may be displaced in the direction of the arrow 14 and rotated around the axis 13). During this rotation around an examination object arranged on the patient table 10, a plurality of projection images of the examination object may be recorded from different projection directions (e.g., angulations). Arranged in the suspension bracket 12, for example, is a slip ring structure, via which the C-arm 11 may be rotated in an endless rotation (e.g., without restrictions relating to the angle of rotation) around the axis 13 (e.g., also in both directions). In many existing x-ray imaging systems, there are restrictions relating to the dynamics for each speed of rotation, which, for example, necessitate a suitable calibration for each speed of rotation. With the introduction of a slip ring in the rotation part of the angulation, the C-arm 11 may rotate without restriction, and the dynamics for each speed of rotation are significantly improved. Different constant speeds of rotation are possible without difficulty.

In addition, the x-ray imaging system has a system controller 15 for actuating system functions (e.g., movements of the recording system or the application of x-ray radiation). Integrated therein or alternatively separate therefrom, there is provision, for example, for an image processing system 20 for processing projection images and for reconstruction of the projection images into volume images, and a computing unit 16 (e.g., a computer). In addition, the x-ray imaging system also has a memory unit 17 (e.g., a memory), an input unit 18 (e.g., an input such as a keyboard or a touch screen), and a display unit 19 (e.g., a display such as a monitor or a touch screen).

Figure 2:
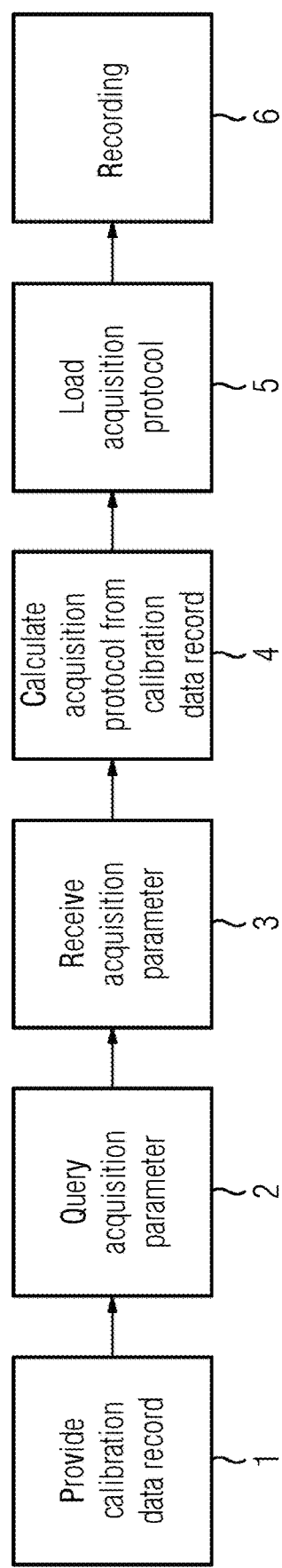
FIG. 2 shows a sequence of a method for acquiring an image data record according to an embodiment.

FIG. 2 shows a sequence of one embodiment of the method. In a first act 1, a calibration data record that has measurement data from a plurality of rotations of the recording system in endless rotation is provided. An initial calibration data record of this kind may be created once and may then be used for all future three-dimensional (3D) or four-dimensional (4D) recordings. The calibration data record may be created as comprehensively as possible and may contain a very high number of calibration data items, where a very fine scanning of the path is performed with as many different speeds of rotation as possible. In this manner, a large number of different sampling points on the trajectory may be available. The calibration data record may be stored in a memory unit or a database and may be retrieved therefrom and provided on demand.

In a second act 2 (e.g., optional), one or more acquisition parameters are queried from the group consisting of period of acquisition, number of projection images to be acquired, and angular region of the acquisition to be recorded for a planned 3D or 4D x-ray recording with the x-ray imaging system. This may be performed via the display unit 19 and the input unit 18, for example. The user may thus be shown one or more selection windows, for example, with the option of performing a free input at this point by the input unit. If the user makes the corresponding input(s) and enters the corresponding acquisition parameters, in a third act 3, the input acquisition parameters are thus received by the x-ray imaging system (e.g., the system controller) and used for further processing (e.g., forwarded to the computing unit 16).

In a fourth act 4, an individual acquisition protocol is subsequently calculated by using the calibration data record and the received acquisition parameters (e.g., by the computing unit). The individual acquisition protocol does not have to be predefined exactly in the calibration data record as such, but may rather be calculated from the available calibration data record in a flexible manner due to the fact that the dynamics for each speed of rotation of the rotation of the recording system are so consistent. Thus, for example, the period of acquisition may be selected freely.

In a fifth act 5, the calculated individual acquisition protocol is subsequently loaded into the x-ray imaging system by the system controller, and in a sixth act 6, the 3D or 4D x-ray recording corresponding with the acquisition protocol is then performed. Further acts, such as the display of image data or image processing and reconstruction, may be performed subsequently.

Via the method and the x-ray imaging system according to one or more of the present embodiments, a user may define acquisition protocols for 3D and 4D x-ray recordings in an interactive manner (e.g., at any time even during an intervention in a patient-specific manner) and starts the corresponding 3D and 4D x-ray recordings directly. The particularity lies in the conversion of a dynamic problem only to be solved by extensive calibration with the aid of an enlargement of the angulation region (e.g., unrestricted) into a simpler path sampling method with constantly calibrated dynamics of the C-arm for each speed of rotation. In one embodiment, a plurality of dynamics (e.g., speeds of rotation) may be used, and each may be calibrated separately. By introducing a slip ring in the rotation part of the angulation, the C-arm may rotate without restriction. Different constant speeds of rotation (and thus dynamics remaining constant for each speed of rotation) may be provided.

By removing the upper barrier of the range of rotation, the period of acquisition may be specified by images being captured for the 3D reconstruction with different intervals on the trajectory, for example. In order to enable this different location sampling, in the initial calibration, the path is sampled very finely (e.g., for each speed of rotation), in order to provide different sampling points on the trajectory. This concept enables further degrees of freedom with regard to the definition of acquisition protocols, which may be specified by the user during the intervention. These degrees of freedom include, for example, the number of projection images to be acquired and the angular region of the scan to be captured.

For a flexible changing of the acquisition protocol (e.g., during interventional procedures), a method is provided for acquiring an image data record with an x-ray imaging system with a recording system that may be rotated around an examination object. The recording system is embodied for an endless rotation, with the following acts: Providing a calibration data record that has measurement data from a plurality of rotations of the recording system in endless rotation; receiving at least one selectable acquisition parameter, for example, from the group of period of acquisition, number of projection images to be acquired, angular region of the acquisition to be recorded, and angular increment between every two sequential projection images; determining (e.g., calculating) an acquisition protocol with the selected acquisition parameter(s) from the provided calibration data record; loading the determined acquisition protocol; and recording an image data record using the determined acquisition protocol.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquiring an image data record with an x-ray imaging system with a recording system that is rotatable around an examination object, the recording system being configured for unrestricted rotations around the examination object, the method comprising:
   providing a calibration data record associated with the x-ray imaging system, the calibration data record having measurement data from a plurality of unrestricted rotations of the recording system around the examination object;
   receiving at least one selectable acquisition parameter;
   determining an acquisition protocol for acquiring an image based on the at least one received acquisition parameter and the provided calibration data record;
   loading the determined acquisition protocol; and
   recording an image data record using the determined acquisition protocol.

2. The method of claim 1, wherein the at least one selectable acquisition parameter includes a period of acquisition, a number of projection images to be acquired, an angular region of the acquisition to be recorded, an angular increment between every two sequential projection images, or any combination thereof.

3. The method of claim 2, wherein the recording system includes a C-arm that has an x-ray detector and an x-ray source, and
   wherein the C-arm is suspended by a slip ring structure in order to perform the unrestricted rotations.

4. The method of claim 3, further comprising performing a query regarding the at least one selectable acquisition parameter, the at least one selectable acquisition parameter including a period of acquisition, a number of projection images to be acquired, an angular region of the acquisition to be recorded, an angular increment between sequential projection images, or any combination thereof.

5. The method of claim 2, further comprising:
   receiving at least one further acquisition parameter, the at least one further acquisition parameter including a period of acquisition, number of projection images to be acquired, an angular region of the acquisition to be recorded, an angular increment between every two sequential projection images, or any combination thereof;
   calculating a further acquisition protocol;
   loading the further acquisition protocol; and
   recording a further image data record from the further acquisition protocol.

6. The method of claim 2, further comprising performing a query regarding the at least one selectable acquisition parameter, the at least one selectable acquisition parameter including a period of acquisition, a number of projection images to be acquired, an angular region of the acquisition to be recorded, an angular increment between sequential projection images, or any combination thereof.

7. The method of claim 2, further comprising receiving and using at least one further acquisition parameter beyond the group consisting of period of acquisition, number of projection images to be acquired, and angular region of the acquisition to be recorded.

8. The method of claim 1, wherein the recording system includes a C-arm that has an x-ray detector and an x-ray source, and
   wherein the C-arm is suspended by a slip ring structure in order to perform the unrestricted rotations.

9. The method of claim 8, further comprising:
   receiving at least one further acquisition parameter, the at least one further acquisition parameter including a period of acquisition, number of projection images to be acquired, an angular region of the acquisition to be recorded, an angular increment between every two sequential projection images, or any combination thereof;
   calculating a further acquisition protocol;
   loading the further acquisition protocol; and
   recording a further image data record from the further acquisition protocol.

10. The method of claim 8, further comprising performing a query regarding the at least one selectable acquisition parameter, the at least one selectable acquisition parameter including a period of acquisition, a number of projection images to be acquired, an angular region of the acquisition to be recorded, an angular increment between sequential projection images, or any combination thereof.

11. The method of claim 1, further comprising:
   receiving at least one further acquisition parameter, the at least one further acquisition parameter including a period of acquisition, number of projection images to be acquired, an angular region of the acquisition to be recorded, an angular increment between every two sequential projection images, or any combination thereof;
   calculating a further acquisition protocol;
   loading the further acquisition protocol; and
   recording a further image data record from the further acquisition protocol.

12. The method of claim 1, further comprising performing a query regarding the at least one selectable acquisition parameter, the at least one selectable acquisition parameter including a period of acquisition, a number of projection images to be acquired, an angular region of the acquisition to be recorded, an angular increment between sequential projection images, or any combination thereof.

13. The method of claim 1, further comprising receiving and using at least one further acquisition parameter beyond the group consisting of period of acquisition, number of projection images to be acquired, and angular region of the acquisition to be recorded.

14. An x-ray imaging system comprising:
a recording system comprising:
an x-ray detector and an x-ray source arranged on a bracket, the recording system being configured to rotate in unrestricted manner around an examination object, wherein the x-ray imaging system is configured to record a plurality of projection images from different projection directions and an image data record in accordance with an acquisition protocol during an unrestricted rotation of the recording system around the examination object;
a system controller configured to provide a previously recorded calibration data record associated with the x-ray imaging system, the previously recorded calibration data record including measurement data from a plurality of unrestricted rotations of the recording system around the examination object, the system controller also being configured to load an acquisition protocol;
an input configured to receive at least one selectable acquisition parameter, the at least one acquisition parameter including a period of acquisition, a number of projection images to be acquired, an angular region of the acquisition to be recorded, an angular increment between every two sequential projection images, or any combination thereof; and
a computer configured to calculate the acquisition protocol for the image data record based on the at least one received acquisition parameter and the provided calibration data record.

15. The x-ray imaging system of claim 14, wherein the bracket is formed by a C-arm, and the C-arm is suspended by a slip ring structure so that an unrestricted rotation of the C-arm is achievable.

16. The x-ray imaging system of claim 15, wherein the input is further configured to receive and use at least one further acquisition parameter beyond the group consisting of period of acquisition, number of projection images to be acquired, angular region of the acquisition to be recorded, and angular increment between every two sequential projection images.

17. The x-ray imaging system of claim 14, further comprising a display configured to display a query relating to the at least one selectable acquisition parameter.

18. The x-ray imaging system of claim 15, further comprising a display configured to display a query relating to the at least one selectable acquisition parameter.

19. The x-ray imaging system of claim 14, wherein the input is further configured to receive and use at least one further acquisition parameter beyond the group consisting of period of acquisition, number of projection images to be acquired, angular region of the acquisition to be recorded, and angular increment between every two sequential projection images.

* * * * *